(12) United States Patent
Decaudin et al.

(10) Patent No.: US 6,692,250 B1
(45) Date of Patent: Feb. 17, 2004

(54) APPARATUS FOR PHOTOACTIVATION OF PHOTOSENSITIVE COMPOSITE MATERIALS UTILIZED PARTICULARLY IN THE DENTAL FIELD

(75) Inventors: Jean-Michel Decaudin, 124, chemin Levun, Velaux (FR), 13880; Michel Lequime, Eguilles (FR); Elisabeth Duret, Fleury d'Aude (FR); Bognard Duret, Grenoble (FR)

(73) Assignee: Jean-Michel Decaudin (FR)

( * ) Notice: Subject to any disclaimer, the term of this patent is extended or adjusted under 35 U.S.C. 154(b) by 0 days.

(21) Appl. No.: 09/499,175

(22) Filed: Feb. 7, 2000

(30) Foreign Application Priority Data

Feb. 5, 1999 (FR) .............................. 99 01657
Sep. 20, 1999 (FR) ............................ 99 11860

(51) Int. Cl.[7] ................................ A61C 3/00
(52) U.S. Cl. ................................................ 433/29
(58) Field of Search ................ 433/29, 215, 229; 362/119, 120; 606/13, 14, 16, 17

(56) References Cited

U.S. PATENT DOCUMENTS 4,221,994 A * 9/1980 Friedman et al. ............ 315/224
5,420,768 A * 5/1995 Kennedy ...................... 362/119
5,634,711 A * 6/1997 Kennedy et al. ............. 362/119
6,200,134 B1 * 3/2001 Kovac et al. .................. 433/29

FOREIGN PATENT DOCUMENTS

WO  9736552 A  10/1997
WO  9935995 A   7/1999

OTHER PUBLICATIONS

Patent Abstracts of Japan; vol. 1996, No. 1; Jan. 31, 1996 & JP 07 240536 A (Shimadzu Corp.), Sep. 12, 1995; Abstract.

* cited by examiner

Primary Examiner—Nicholas D. Lucchesi
(74) Attorney, Agent, or Firm—Ostrolenk, Faber, Gerb & Soffen, LLP

(57) ABSTRACT

Apparatus for allowing the photoactivation of photosensitive composites used especially in the dental field: A case containing a power supply unit electrically controlled by a central electronic processing unit. A light source connected to the supply unit and which is formed by a plurality of light-emitting diodes. The diodes are associated with a concentrating device making it possible to concentrate in an optimal manner, at a given point, the light emanating from all the emissive areas of the diodes. The concentrating device includes a respective optical fiber associated with each light emitting diode.

15 Claims, 5 Drawing Sheets

APPARATUS FOR PHOTOACTIVATION OF PHOTOSENSITIVE COMPOSITE MATERIALS UTILIZED PARTICULARLY IN THE DENTAL FIELD

FIELD OF THE INVENTION

The present invention relates to an apparatus allowing the photoactivation of photosensitive composites used especially in the dental field.

BACKGROUND OF THE INVENTION

In the dental field, the composites consist of a photocurable resin which reacts to light by modification of its molecular layers or by thermal transformation of its molecules. These two phenomena, which may combine, are dependent on the wave length of the emitted radiation and also on the absorptivity of the composite and have the effect of activating its photoinitiators and of obtaining a substance having the mechanical properties and esthetic characteristics defined according to the dental application.

Photocuring apparatuses generally consist of a case containing an emitting source controlled by an electronic circuit which includes a timer allowing the exposure time to be optimized so as to minimize the heat-up of the tissues surrounding the region to be treated. Moreover, in order to be certain of covering the photosensitive spectral range of the material used and of delivering enough energy to the reaction, these apparatuses use lamps whose emission spectrum is very wide, in combination with filters.

Among the various light sources, mercury vapor lamps have been used, but these emit too much ultraviolet radiation which is dangerous to the patient's eyes.

To avoid this drawback, these lamps have been replaced with halogen lamps. However, these lamps, the lumen/watt ratio of which is low, require the area: to be treated to be exposed for a long period, forcing the patient to keep his mouth open for a long time. Moreover, this overexposure is accompanied by the lamp heating up, requiring the use of noisy and bulky cooling systems.

To remedy these drawbacks, plasma arc lamps having a better lumen/watt efficiency are used at the present time, and part of their spectrum, between 430 and 490 nm, is used, thereby making it possible to significantly increase the energy delivered and to have the required power for rapid curing. However, this increase, in the power is accompanied by a strong increase in the heat dissipated.

In the apparatuses known to date, firstly the conversion of the electrical energy into light energy is mediocre and secondly the cooling systems are noisy and complex, thereby increasing the cost of the apparatus.

Document JP 07240536 describes a light source for a photocuring apparatus consisting firstly of light-emitting diodes which emit radiation between 380 nm and 430 nm and secondly of a concentrating device comprising optical fibers, opposite the entry face of each of which one of said diodes is placed.

However, the concentrating device of this type of apparatus does not allow optimum concentration of the light emanating from the diodes to be achieved since the latter are provided with a lens and because the fiber is in contact with this lens, so there is rapid curing of the materials because of poor coupling between said diodes and the optical fibers.

OBJECT OF THE INVENTION

The object of the present invention is to remedy these drawbacks by proposing an apparatus for photocuring composites and substances for the whitening of teeth, making it possible to carry out rapid and gradual photocuring of the various layers of the material to be treated while allowing the heat dissipated to be significantly reduced.

The photocuring apparatus according to the invention is of the type comprising a case containing a power supply unit electrically controlled by a central electronic processing unit, a light source connected to the supply consisting of a matrix of light-emitting diodes and a device for concentrating the light emanating from the diodes, and is essentially characterized in that:

in a first embodiment, the concentrating device makes it possible to juxtapose, at a given concentration point, the light emanating from all the emitting surfaces of the diodes and consist of optical fibers associated with the light-emitting diodes so that the emitting area of a diode is optically matched as far as possible with the entry area of one or more corresponding optical fibers;

in a second embodiment of the invention, the device for concentrating the light emanating from the diodes makes it possible to superpose, at a given concentration point, the images of all the emitting surfaces of the diodes and consists, on one side, of a collimation device composed of a plurality of convergent lenses each placed in front of the emitting surface of a light-emitting diode in such a way that the emitting surface is at the object focus of the corresponding lens and in such a way that the rays are refracted parallel to the axis of the latter and, on the other side, a focusing device formed from a convergent lens of suitable dimensions in order to allow the parallel incident rays emanating from the collimation device to be refracted toward the concentration point which is the focus of the lens.

The collimating or focusing lenses may be of the refractive, diffractive (Fresnel lenses, holographic, binary lenses) or stepped-index type, or a combination of these various types of lenses. The focusing lenses will preferably be of the reflective type.

The given point where the light emanating from the diodes at the exit of the concentrating device is concentrated may be the entry face of a waveguide provided with an endpiece for applying the light coming from the light source to the region to be treated or it may be, directly, the region to be treated.

According to the invention, the diodes are optically matched as far as possible with the corresponding fiber or fibers by positioning the entry surface of the corresponding fiber in contact with the emission surface of the diode or in the immediate vicinity of the latter and by maintaining a ratio between the emitting area of the diode and the entry area of the fiber or fibers facing it as close as possible to 1.

The optical matching may also be accomplished by forming the image via an imaging optic which images the emissive area of the diode onto the entry face of one or more fibers, while keeping an area ratio as close as possible to 1.

In a preferred embodiment of the concentrating device consisting of optical fibers, the diodes are arranged in a regular manner on a plate and the optical fibers are each inserted into a hole having a diameter slightly greater than the diameter of said fibers and made in a plate positioned by alignment means near the support plate for the diodes and the pitch of the holes of which is equal to that of said diodes.

According to an additional feature of the invention the supply to the light-emitting diodes may be controlled manually by means of control knobs or automatically by means of the central processing unit containing in its memory the parameters inherent to the control of said diodes making it possible to obtain various power profiles.

According to another additional feature of the invention, the power supply to the diodes can be regulated in pulsed mode so as to obtain higher instantaneous powers, this being favorable for particular curing applications.

According to another additional feature of the invention, the light output by the bundle of optical fibers has at least two wavelengths lying preferably around 380 or 475 µm and 750 µm, so as to obtain both radiation necessary for certain composites and radiation suitable for thermal action on the substances intended for the whitening of teeth.

According to another additional feature of the invention, the core of the optical guide in which the light output by the concentrating device propagates may be made of plastic, of glass or it may be liquid.

BRIEF DESCRIPTION OF THE DRAWINGS

The advantages and the features of the present invention will become more clearly apparent from the description which follows and which relates to the appended drawing, which shows several nonrestrictive embodiments thereof.

DETAILED DESCRIPTION OF THE DRAWINGS

Figure 1:
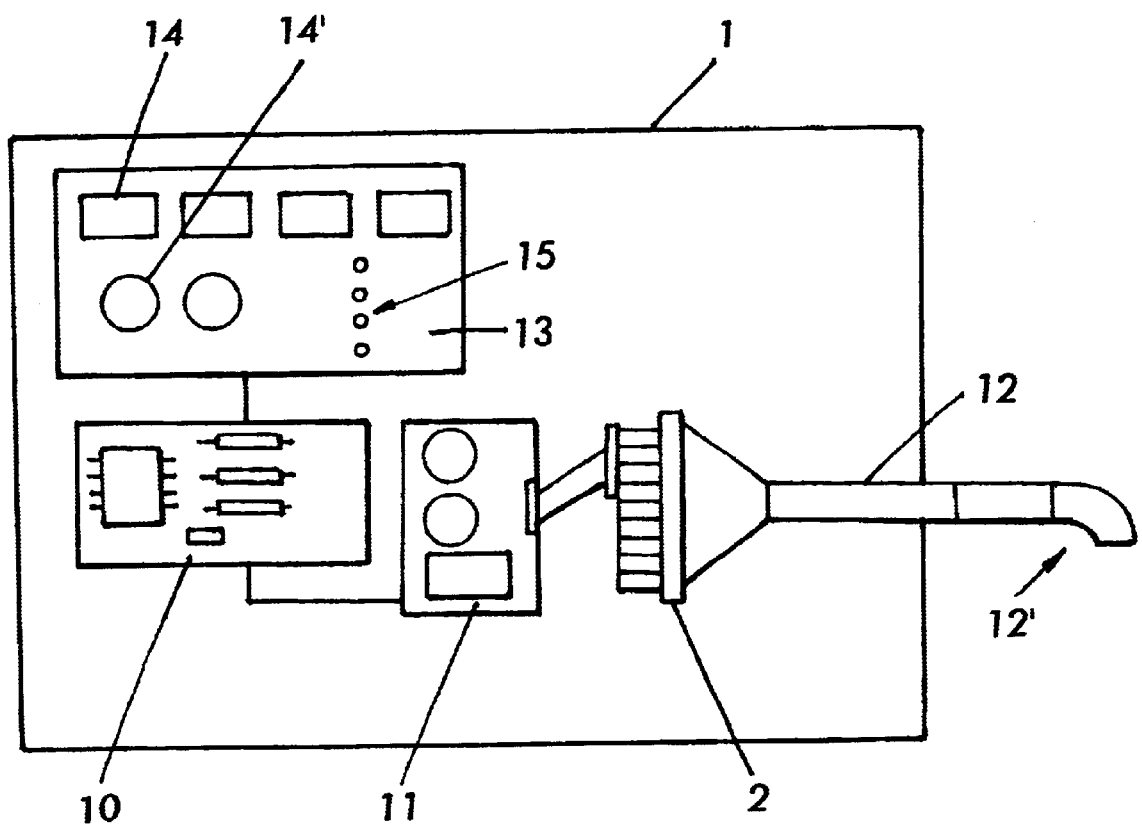
FIG. 1 shows the block diagram of the device according to the invention.

Referring to FIG. 1, it may be seen that an apparatus intended for the photocuring of composites and for the photoactivation of substances intended for the whitening of teeth consists of a case 1 housing a central electronic processing unit 10 electrically connected to a power supply 11 and of a light source 2 generating light intended to be applied, by means of a waveguide 12 terminating in a right-angled endpiece 12', to a region to be treated, not shown.

The central processing unit 10 is also electrically connected to an interface 13 having control buttons 14 and 14' and indicator lights 15 allowing the operator to communicate with the apparatus and especially to adjust the parameters inherent to light emission.

Figure 2A:
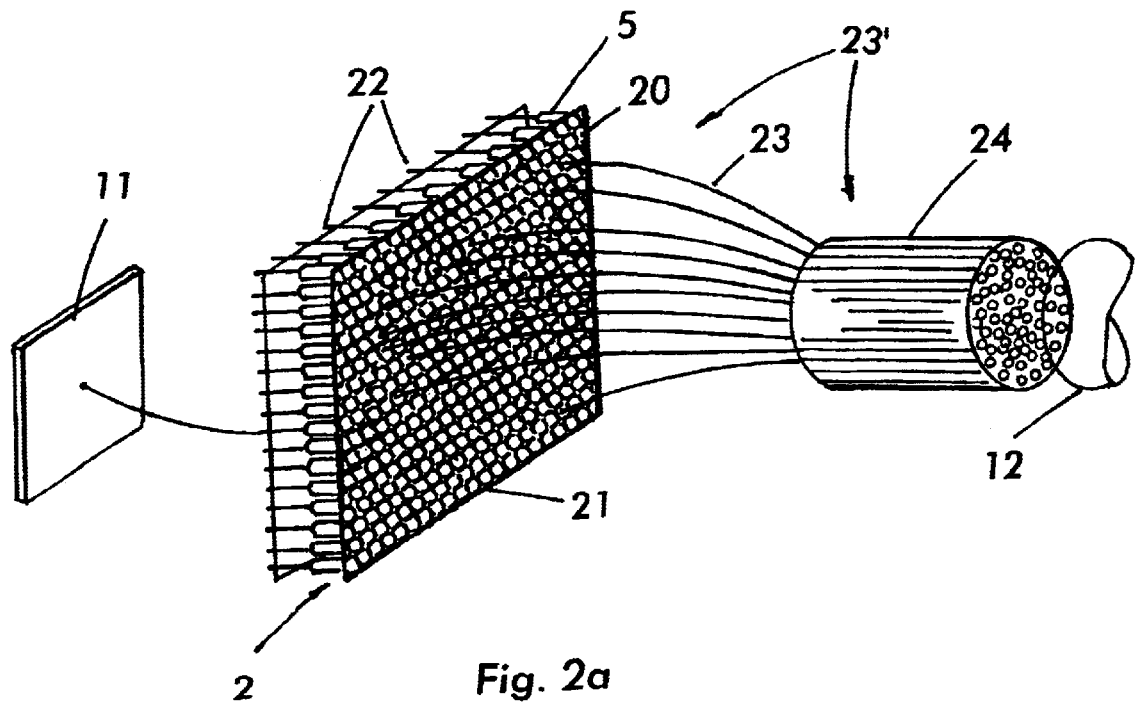
FIG. 2a shows a perspective view of the light source consisting of a multiplicity of light-emitting diodes associated with a concentrating device consisting of optical fibers.

Referring now to FIG. 2a, it may be seen that the light source 2 comprises a plurality of light-emitting diodes 20 which are associated with a concentrating device 23' and are arranged in a regular manner in the form of a matrix, these being fastened to a support 21, for example by adhesive bonding, provided with electrical connections 22 allowing the diodes 20 to be connected to the power supply unit 11. The concentrating device 23 allows the light emanating from the diodes 20 to be concentrated at a given point which may be the entry face of the waveguide 12 or directly the region to be treated. The concentrating device 23' consists of a bundle of optical fibers 23, for each optical fiber 23 of which one of the ends is placed and held facing the emitting surface of a light-emitting diode 20 so as to collect the light wave that it emits.

It may also be seen that the optical fibers 23 are joined together and held against one another in a ring 24 making it possible to obtain, at the exit of the concentrating device 3 formed by all the exit faces of the fibers 23, an emission surface of small dimensions, the light output from which will be conveyed through the waveguide 12 which has approximately the same diameter as the diameter of the ring 24.

Figure 2B:
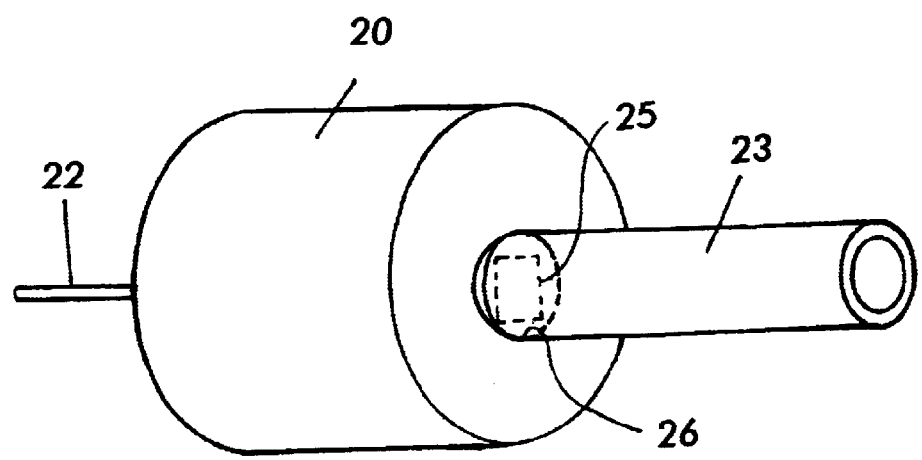
FIG. 2b shows a detailed view of the coupling of a diode with an optical fiber.

FIG. 2b shows a light-emitting diode 20 having an emission surface 25 lying facing and in the immediate vicinity of or in contact with the entry surface 26 of an optical fiber 23 coupled to said diode 2 and the dimensions of the entry surface 26 of the fiber 23 of which are approximately identical to those of the emission surface 25 of the diode 20 so as to collect as much as possible from the active part of the emission surface 25 of the diode 20.

The optical fibers 23 may be inserted into holes made in a plate, with a hole pitch more or less identical to the distribution pitch of the diodes 20.

Consequently:

on the one hand, because of the ratio between the emitting area of a diode and the entry area of the fiber facing it and on the other hand, because the emission surface of a diode is positioned in contact with or in the immediate vicinity of, that is to say almost in contact with, the entry surface of the fiber facing it, giving very good coupling between the diodes and the fibers, the concentration obtained at the exit of the fibers 23 is optimal, thereby making it possible to carry out rapid curing particularly suitable in the field of the photo-curing of dental composites.

Figures 6A, 6B:
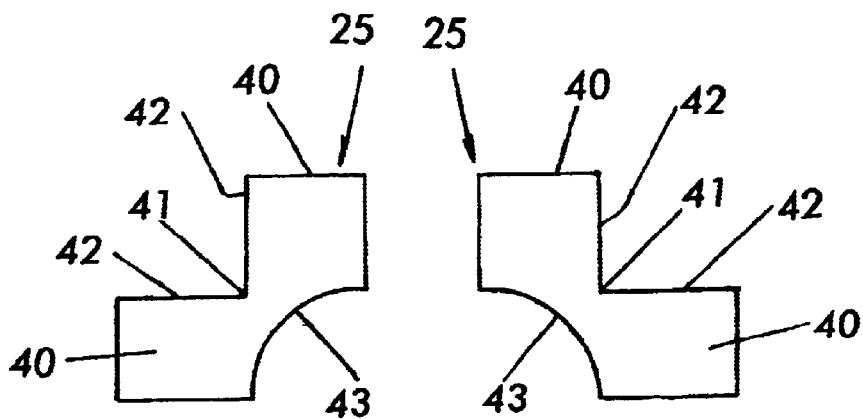
FIG. 6a shows one particular shape of the emitting surface of a light-emitting diode.
FIG. 6b shows the particular shape of the emitting surface of the previous figure in a different orientation.

It will be noted that several fibers may be associated with a single diode, especially when the diode has a particular emission surface having several emitting surface portions such as, for example, two juxtaposed square surfaces (FIGS. 6a and 6b). In this case, each emitting surface portion will then be associated with one optical fiber, while respecting the above-mentioned optical matching parameters.

The optical fibers 23 may be inserted into the holes made in a plate, with a hole pitch more or less identical to the distribution pitch of the diodes 20.

The light-emitting diodes 20 will preferably be of the type without an optical coupling lens in order to bring the fiber as close as possible to the emissive surface of the diode and the optical fibers 23 will preferably be fibers which have a large numerical aperture, in order to capture the maximum amount of light emitted by the light-emitting diodes 20, and have a low linear attenuation in the wavelength ranges used.

The waveguide 12 may be a liquid optical fiber having a very low line loss and offering good homogenization of the light emanating from the diodes 20 via the optical fibers 23.

The light-emitting diodes 20 may be electrically controlled, either manually at the interface 13 by actuating buttons 14 provided for this purpose, or via the central processing unit 10 by means of a program for controlling the power of the diodes 20 by acting on the supply unit 11 for the latter.

Consequently, the diodes 20 may be supplied with power, on an on/off basis, individually or per packet of diodes having the same emission spectrum, so as to be able to modify the emission spectrum of the resulting light output by the strand 24. It is also possible to modify the overall emission spectrum by varying the intensity off the electrical current flowing through the diodes 20, this variation being accompanied by a variation in the power emitted by the diode 20, which causes a variation in the overall spectrum.

Thus, the variation in current in an array of diodes 20 of a given spectral type will result in a modification of the emission power of the diodes 20 and therefore a variation in the spectrum of the resulting light output by the set of optical fibers 23, just as interrupting the supply to the diodes of one of its arrays will, by eliminating a spectrum, modify the spectral components of the resulting light output by the filters [sic] 23.

Figure 3A:
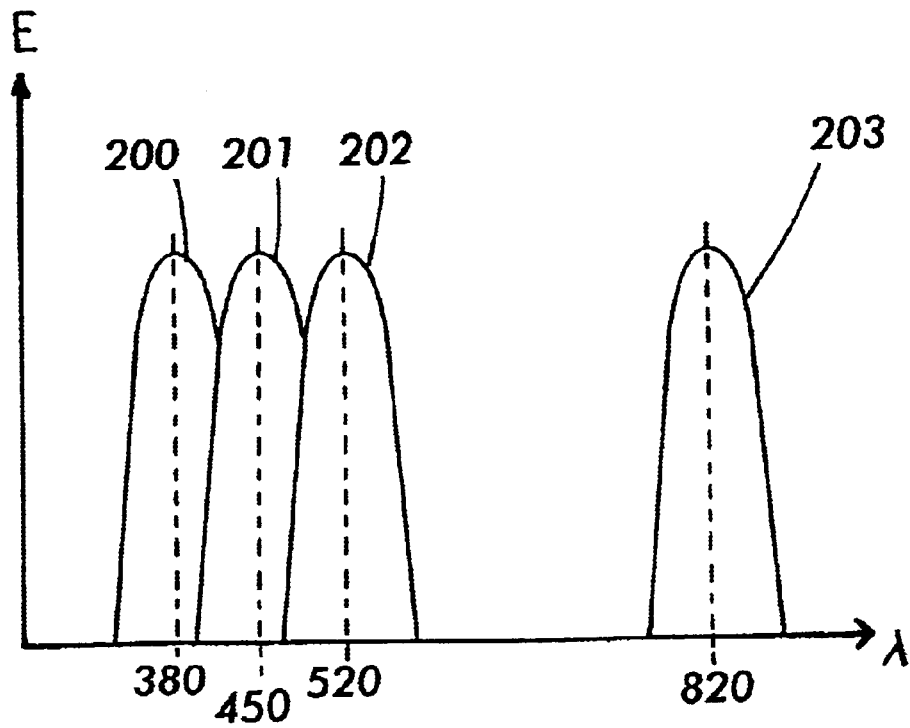
FIG. 3a shows the emission spectrum from four light-emitting diodes having different spectral components.

FIG. 3a shows four curves 200, 201, 202, 203, each representing the emission spectrum of one type of light-emitting diode 20 having a wavelength of 380, 450, 520 and 820 nm, respectively, for which the light emission is a maximum.

In this case, the light-emitting diodes 20 whose spectrum lies around 380 nm are particularly suitable for the treatment of materials which are more sensitive to ultraviolet light, whereas the light-emitting diodes whose spectrum lies around 450 nm are suitable for the treatment of composites within the family, for example, of camphoroquinones, and the diodes whose spectrum lies around 820 nm allow a thermal action on whitening products.

Figure 3B:
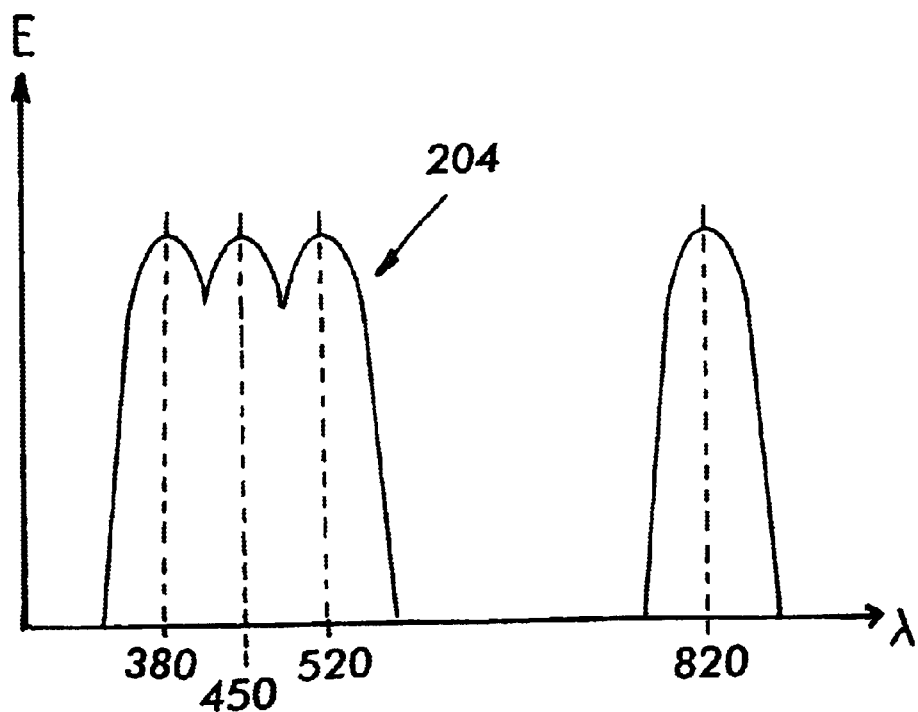
FIG. 3b shows the overall spectrum resulting from the addition of the light emissions from the above four diodes.

Thus, the choice of the spectral characteristics of the light emitted by the light-emitting diodes makes it possible to obtain the desired spectral profile 204 (FIG. 3b) depending on the application, by adding the light emitted by the various diodes 20. Consequently, unlike the current systems which do not have a matrix of light-emitting diodes, the apparatus according to the invention makes it possible to obtain the desired spectral profile, by the addition of light, and therefore without filters, and the entire amount of light emitted.

It will be noted that because the light-emitting diodes 20 have a low electrical current consumption, the device may be supplied with energy from batteries, which may or may not be rechargeable.

Advantageously, the light-emitting diodes 2 may be fastened to an interchangeable support provided with connectors, allowing, it to be rapidly connected to the apparatus according to the invention.

Moreover, so as to be able to modify the energy profiles stored by the manufacturer in the read-only memory of the central processing unit 10 which may be remotely programmed by the user, for example by means of a memory card of the smart card type containing the program including the parameters inherent to the electrical control of the diodes. [sic]

The remote programming of the microprocessor, which may also be carried out by means of a microcomputer via a modem-type interface, also allows the composite manufacturer to optimize the action spectrum of the light source according to his material and to provide an after-sales or update service very rapidly and very simply.

Trials have shown that, in order to obtain curing that is rapid and desirable both from the clinical and biological standpoints, the illumination provided by the light source 2 must lie between 1 and 2 W/cm$^2$ and preferably around 1.5 W/cm$^2$. This illumination is in direct relation with the number of light-emitting diodes 20 and the power which is delivered to them by the supply card 11.

Figure 4:
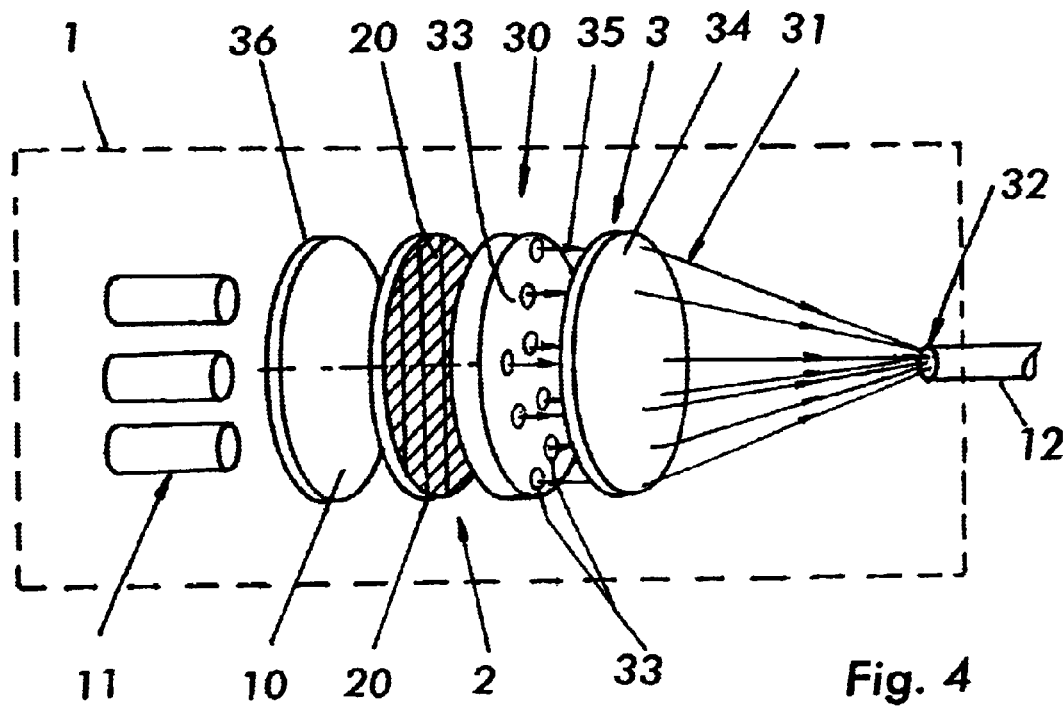
FIG. 4 shows a perspective schematic view of the concentrating device in another embodiment.
Figure 5:
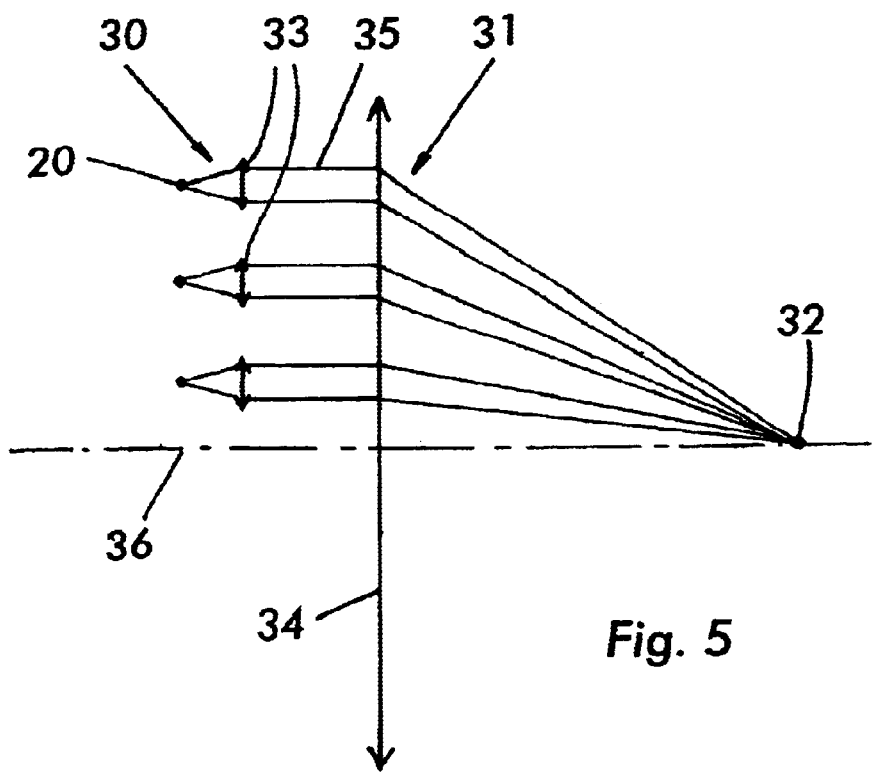
FIG. 5 shows the optical diagram of the concentrating device of the previous figure.

Referring now to FIGS. 4 and 5, these show, in another embodiment, a concentrating device 3 consisting of a collimating device 30 and of a focusing device 31 allowing the light rays emitted by the light-emitting diodes 20 of a lightsource 2 to be collimated and allowing all these rays to be concentrated on a given concentration point 32 corresponding substantially either directly to the treatment area or to the entry face, of the waveguide 12.

The collimating device 30, which lies facing the light-emitting diodes 20, consists of a matrix of convergent lenses 33 which is defined in such a way that these lenses are each positioned so as to face the emitting surface of alight-emitting diode 20 and at a distance such that the diode 20 lies at the object focus of the corresponding lens 33. The focusing device 31 comprises a convergent lens 34, parallel to the plane containing the lenses 33 and to the plane containing the diodes 20, having approximately the same dimensions as those of the matrix 30 of lenses 33. The convergent lens 34 has an, image focus corresponding approximately to the entry face of the waveguide 12 where the incident rays 35, parallel to the main axis 36 of the convergent lens 34 and to the optical axes of the convergent lenses 31 of the collimating device 30, are refracted.

The light-emitting diodes 20 known at the present time have emitting surfaces 25 whose shape may be simple, such as a square for example, or, as may be seen in FIG. 6a, may be complex, having several emitting surface portions, such as, for example, two square emitting surfaces 40 joined via one of their corners 41 and of which two adjacent sides 42, joined by this point, form a circular arc 43. FIG. 6b showing [sic] the same pattern as that in FIG. 3a but with a different orientation, the latter being rotated through 90° with respect to the axis of the corresponding diode 20.

Figure 7:
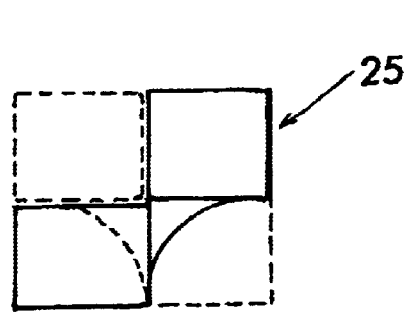
FIG. 7 shows the superposition of the images at the image focus of the optical device.

FIG. 7 shows the optical resultant at the image focus 32 corresponding to a superposition of patterns which correspond to those of FIGS. 6a and 6b and of which some are oriented according to the illustration in FIG. 6a and others according to the illustration in FIG. 6b.

Figure 8:
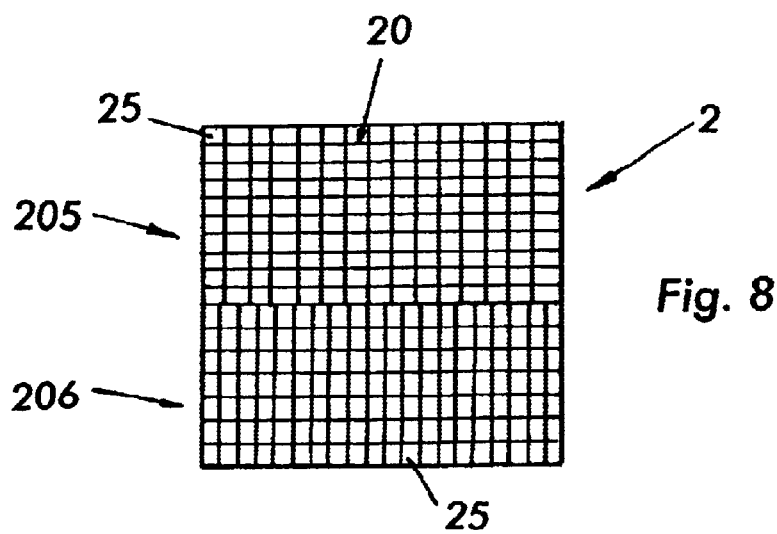
FIG. 8 shows a light source composed of photon emitters having emission surfaces of identical shape and in two different orientations.

FIG. 8 shows a light source 2 consisting of a series 205 of light-emitting diodes 20 of rectangular shape and oriented in one direction and a series 206 of diodes 20 of the same type but oriented which each have an emission surface 25 of rectangular shape and a series 206 of diodes 20 all having the same emission surface 25 but oriented differently, and especially rotated through 90° with respect to the emission axis of the corresponding diode 20. [sic]

The source 2 may consist of a light-emitting diode 20 of different wavelength.

Figure 9:
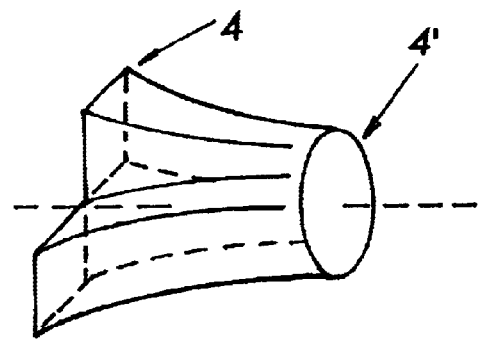
FIG. 9 shows a perspective view of an anamorphosis of an image of a certain shape.

FIG. 9 shows that the shape of an image at the exit of the concentrating device produced according to one 23' or other 3 of the embodiments described above can be modified by a device known in the anamorphosing art, which transforms, for example, a complex image 4, like that in FIG. 6a or FIG. 6b, into a circular image 4'; the device performing this anamorphosis could be placed between the image focus of the concentrating device and the surface to be treated or the entry face of the waveguide.

What is claimed is:

1. An apparatus allowing the photoactivation of photosensitive composites comprising: a case containing a power supply unit electrically controlled by a central electronic processing unit, a light source connected to the power supply unit and having a matrix of light-emitting diodes, and a device for concentrating the light emanating from the light-emitting diodes and having a plurality of optical fibers, each of the light-emitting diodes having a respective emitting surface aligned with an entry area of at least one optical fiber and optically coupled to the entry area without a light-shape altering device so that the respective emitting surface is optically matched with the entry area of the at least one optical fiber, whereby the device for concentrating focuses the light from the emitting surface of all the light-emitting diodes at a given concentration point.

2. An apparatus according to claim 1, an imaging optic image of the respective emitting surface of the light-emitting diode is directed onto the entry area of the at least one optical fiber surface which covers this image in a ratio as close as possible to 1:1, the entry area of the at least one fiber being either in direct contact with or located in the immediate vicinity of the respective emitting surface of the light emitting diode.

3. An apparatus allowing the photoactivation of photosensitive composites comprising: a case containing a power supply unit electrically controlled by a central electronic processing unit, a support plate, a light source connected to the power supply unit and having a matrix of light-emitting diodes which are mounted on the support plate, a guide plate located opposite to the support plate and having an array of holes, and a device for concentrating the light emanating from the light-emitting diodes and having a plurality of optical fibers each of which is inserted into a respective hole of the guide plate, a diameter of each hole being slightly greater than a diameter of a respective optical fiber and a pitch of each hole being equal to that of the light-emitting diode.

4. The apparatus according to claim 3, wherein the power supply unit to the light-emitting diodes may be controlled manually by means of control knobs or automatically by means of the central processing unit containing in its memory the parameters inherent to the control of the diodes making it possible to obtain various power profiles.

5. The apparatus according to claim 3, wherein the power supply unit to the light-emitting diodes can be regulated in pulsed mode so as to obtain higher instantaneous powers.

6. The apparatus according to claim 3, further comprising an optical guide having a core in which the light output by the device for concentrating propagates, the core being made of plastic or glass, or being liquid.

7. An apparatus according to claim 3, wherein the emitting surface of each light-emitting diode has the shape of a square or of a rectangle, or has a complex shape.

8. An apparatus according to claim 7, wherein the emitting surface is composed of two squares joined to one another so that each has a free corner connected to another free corner by a circular arc.

9. The apparatus according to, claim 3, wherein the matrix consists of the light-emitting diodes arranged in two sub-arrays which have identically shaped emitting surfaces oriented so that the light-emitting surfaces of light-emitting diodes of one of the two sub-arrays are oriented differently from the light-emitting surfaces of light-emitting diodes of the other sub-array.

10. The apparatus according to claim 9, wherein the emitting surfaces of the light-emitting diodes of one of the two sub-arrays are rotated through 90° with respect to the emitting surfaces of the light-emitting diodes of the other sub-array.

11. The apparatus according to claim 3, further comprising a device which anamorphoses the image formed from the superposition of the images of the emitting surfaces of the light-emitting diodes at the exit of the device for concentrating the light.

12. The apparatus according to claim 11, wherein the concentration point at the exit of the device for concentrating the light is either the entry face of a waveguide or directly the region to be treated.

13. An apparatus allowing the photoactivation of photosensitive composites comprising:
 a case containing a power supply unit electrically controlled by a central electronic processing unit, a light source connected to the supply unit which is comprised of a matrix of light-emitting diodes and a device for concentrating the light emanating from the diodes and having a collimating device composed of a plurality of smaller convergent lenses each placed in front of the emitting surface of a respective light-emitting diode in such a way that the light-emitting surface is at the object focus of the corresponding smaller convergent lens and in such a way that the rays are refracted parallel to the axis of the corresponding smaller convergent lens, and a focusing device formed from a larger convergent lens dimensioned to allow the incident rays emanating from the collimating device to be refracted toward the concentration point which is the focus of the larger convergent lens.

14. The apparatus according to claim 13, wherein the smaller and larger lenses are of the refractive, diffractive or stepped-index type, or a combination of these various types of lenses.

15. The apparatus according to claim 13, wherein the larger lense is a focusing lense which is of the reflective type.

* * * * *